United States Patent [19]

Han

[11] Patent Number: 5,538,614
[45] Date of Patent: Jul. 23, 1996

[54] MACROMOLECULE RECOVERY CASSETTE

[76] Inventor: Dawn D. Han, 1 Coleman St. #2A, West Haven, Conn. 06516

[21] Appl. No.: 291,770

[22] Filed: Aug. 17, 1994

[51] Int. Cl.[6] .............................. B01D 57/02; G01N 27/26
[52] U.S. Cl. ........................ 204/613; 204/606; 204/456; 204/462
[58] Field of Search ............................... 204/299 R, 301, 204/182.3, 182.6, 182.8, 456, 462, 606, 613

[56] References Cited

U.S. PATENT DOCUMENTS

| 4,049,534 | 9/1977 | Posner | 204/299 R |
| 4,608,147 | 8/1986 | Clad | 204/301 |
| 4,634,513 | 1/1987 | Asao | 204/299 R |
| 4,699,706 | 10/1987 | Burd et al. | 204/301 |
| 4,725,348 | 2/1988 | Diekmann | 204/299 R |
| 4,747,918 | 5/1988 | Wassenberg II | 204/299 R |
| 4,948,481 | 8/1990 | Müllner | 204/182.8 |
| 4,964,961 | 10/1990 | Brautigam | 204/182.3 |
| 5,217,591 | 6/1993 | Gombocz et al. | 204/299 R |
| 5,217,593 | 6/1993 | MacDonnell | 304/299 R |
| 5,384,022 | 1/1995 | Rajasekaran | 204/299 R |

FOREIGN PATENT DOCUMENTS

| 6170175 | 6/1994 | Japan . | |
| 9015148 | 12/1990 | WIPO | C12P 19/34 |

OTHER PUBLICATIONS

N. Blin et al., "Isolation of Large Molecule Weight DNA from Agarose Gels for further Digestion by Resinction Enzymes", Apr. 1975, FEBS letters V53, No. 1 84–86.

Udo Wienand et al., "Electrophoretic Elution of Nucleic Acids for Gels Adapted for Subsequent Biological Tests", Feb. 1979, FEBS letters, V.98, No.2 , 319–323.

R. W. J. Thurling et al., "A Freeze –Squeeze Method for Recovering Long DNA from Agarose Gels,"Analytical Biochemistry 66, 213–220 (1975).

A. Clad et al., "A Cheap, Time–and DNA Saving Device for the Electrophoretic Elution of DNA from Gels", Analytical Biochemistry 124, 299–302 (1982).

J. Samgrook et al., "Molecular Cloning", Cold Spring Harbor Laboratory Press, 1989, pp. 6.22–6.46.

F. M. Ausable et al., "Current Protocols in Molecular Biology ",John Wiley & Sons, New York, 1991, pp. 2.6.1–2.7.5.

*Primary Examiner*—John Niebling
*Assistant Examiner*—Alex Noguerola

[57] ABSTRACT

An elution cassette is invented for macromolecule recovery from electrophoresis gels. The cassette comprises a frame (10), a front barrier (20), a back barrier (30), and a space inside the cassette (35) defined by the frame and the barriers. The barrier made of filter materials allows macromolecules to pass through while stopping gel debris. The back barrier is made of a membrane material allowing small ions to pass through but not macromolecules. When the cassette is inserted into an agarose gel and the electrophoresis is continued, macromolecules driven by an electric field migrate into the cassette through the front barrier and are stopped by the back barrier. The macromolecules contained in the space between the barriers can then be recovered.

3 Claims, 3 Drawing Sheets

MACROMOLECULE RECOVERY CASSETTE

BACKGROUND OF THE INVENTION (1) Field of the Invention

This invention relates to the techniques to recover macromolecules, specifically to recover DNA molecules from agarose gels.

(2) Description of the Prior Art

In laboratories, DNAs are frequently cut into fragments with enzymes and separated by agarose gel electrophoresis. In the electrophoresis process, charged DNA fragments migrate towards the positive electrode through agarose gel matrix submerged in electrophoresis buffer. A smaller fragment, having less resistance in an agarose gel, migrates faster than a larger one and thus is separated from the latter. DNA recovery from agarose gels is an essential step in the recombinant DNA technology. In the 1970s, protocols for DNA recovery from agarose gels were published. Among the protocols, the following were relatively successful: the freeze-squeeze method (Thuring, R. W. J., et al., Anal. Biochem. 66, 213–220, 1975), gel dissolution using potassium iodide (Blin, N., et al., FEBS lett. 53, 84–86, 1975), electroelution (Wienand, U., et al. FEBS Lett. 98, 319–323, 1978), and the techniques involving binding of DNA to powdered glass. The freeze-squeeze method, less efficient especially for larger fragments, is seldom used nowadays. The other methods have been modified and improved. The most used methods for DNA recovery from agarose gels are described in detail in "CURRENT PROTOCOLS IN MOLECULAR BIOLOGY" (Ausubel, F. M., et al., John Wiley & Sons, New York, 1991, pp. 2.6.1–2.7.5) and "MOLECULAR CLONING" (Samgrook, J., et al. Cold Spring Harbor Laboratory Press, 1989, pp. 6.22–6.46), two standard manuals used in almost all labs involving in recombinant DNA techniques or molecular biology. Six commonly used methods are listed below (three methods described in the two lab manuals and three commercially available products):

Electroelution into dialysis bags,

Electrophoresis onto diethylaminoethyl (DEAE)-cellulose membrane,

Low-melting temperature agarose gel method,

Gelase digestion method (Epicentre Technologies, Madison, Wisc.)

GENECLEAN kit (Bio 101 Inc. La Jolla, Calif.),

SpinBind method (FMC BioProducts, Rockland, Me.).

Electrophoresis onto DEAE-cellulose method is not suitable for very large or very small DNA fragments. Low-melting gel method is less reproducible and labor intensive. Gelase digestion method requires a long incubation time (12–16 hours). The procedures of GENECLEAN kit and SpinBind are complicated and very technique dependent. In addition, these methods require temperature-controlled water bath, or chromatographic columns, or additional chemicals that are toxic to the environment.

Electroelution into dialysis bag method is particularly appropriate for the recovery of a wide size range of DNA fragments and large amount of DNA, and it is very reproducible and reliable. But the method is very inconvenient, and a significant amount of DNA can be lost. Therefore it is recommended to be used only when necessary for large DNA fragment recovery which is inefficient by other techniques (Current Protocols, and Molecular Cloning). The inconvenience and the significant DNA loss of this method are due to the awkward procedure and the large volume of buffer in which DNAs are eluted.

An article in the journal of Analytical Biochemistry 124, 299–302 (1982), U.S. Pat. No. 4,725,348 to Diekmann (1988), U.S. Pat. No. 4,948,481 to Mullner (1990), U.S. Pat. No. 4,608,147 to Clad (1986), and U.S. Pat. No. 4,964,961 to Brautigam et al. (1990) disclosed several apparatuses for electroeluting charged macromolecules. They are all rather complicated and not very easy to use. Therefore they are seldom seen in laboratories.

All the above methods are not satisfactory. Simpler and better methods are long awaited. The current invention meets this demand. In this invention, an elution device, a disposable cassette, is designed based on the same principle of electroelution into dialysis bag method. Since the procedure is simplified and elution volume is minimized, the new invention retains all advantages and eliminates the disadvantages of the method of electroelution into dialysis bag.

SUMMARY

The currently used methods to recover DNA fragments from gels are all rather complicated and/or time consuming. A disposable elution cassette is invented based on the principle of electroelution. The cassette can be inserted directly into an agarose gel beside a DNA band. The DNA band can then be run into the cassette and recovered with a brief electrophoresis. The invention makes DNA recovery very easy, simple, fast, high in recovery yield, and still reliable, reproducible and effective for DNA of all sizes.

OBJECTS AND ADVANTAGES

The objects and advantages of the present invention are to provide an elution cassette for macromolecule recovery from electrophoresis gels (1) with a simpler procedure;

(2) which requires less time;

(3) which is very easy to operate;

(4) which does not require a temperature-controlled water bath;

(5) which does not require a chromatographic column;

(6) which does not require the addition of chemicals that are toxic to the environment;

(7) which does not require special type of agarose gels;

(8) which is suitable for virtually all sizes of DNA molecules (>10 bp);

(9) which is particularly appropriate for recovering larger amount (>500 ng) of DNA;

(10) which is high in recovery yield thus suitable for small amount of DNA.

BRIEF DESCRIPTION OF DRAWINGS

In the drawings, typical embodiments of the elution cassette are shown.

Figure 1A:
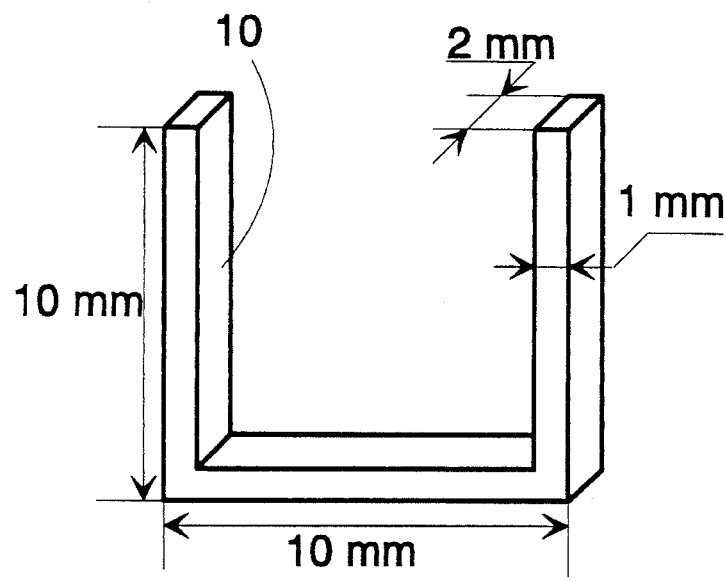
FIG. 1A shows frame 10 of the cassette.

| Reference Numerals In Drawings | |
|---|---|
| 10 frame | 20 front barrier |
| 30 back barrier | 35 space inside the cassette |
| 40 top bar | 42 DNA bands |
| 44 agarose gel | 46 electrophoresis apparatus |
| 48 DNA loading wells | 50 electrodes |
| 52 invented cassette | 54 pipette |

DESCRIPTION OF THE PREFERRED EMBODIMENTS—FIG. 1A TO 1D, 2A AND 2B

Figure 1C:
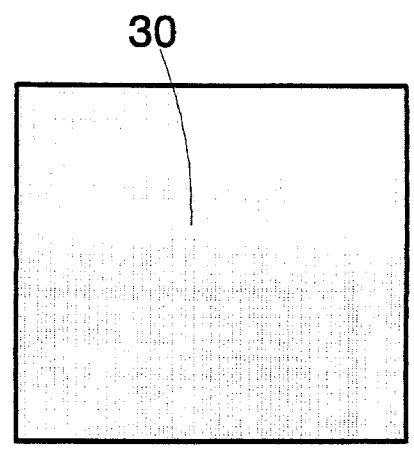
FIG. 1C shows back barrier 30 of the cassette.
Figure 1B:
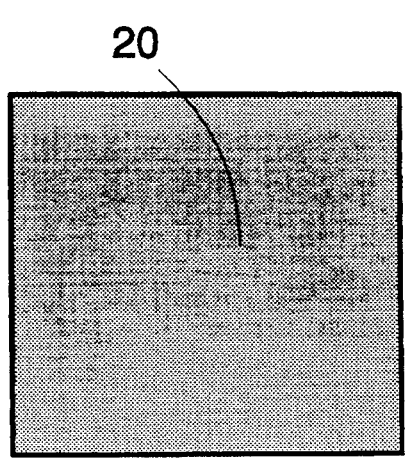
FIG. 1B shows front barrier 20 of the cassette.
Figure 1D:
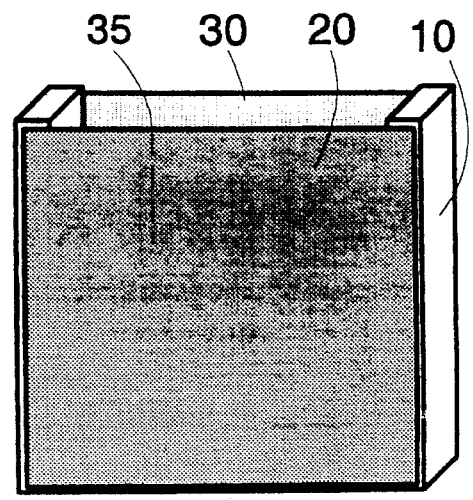
FIG. 1D shows the cassette with the barriers attached to the frame.
Figure 2A:
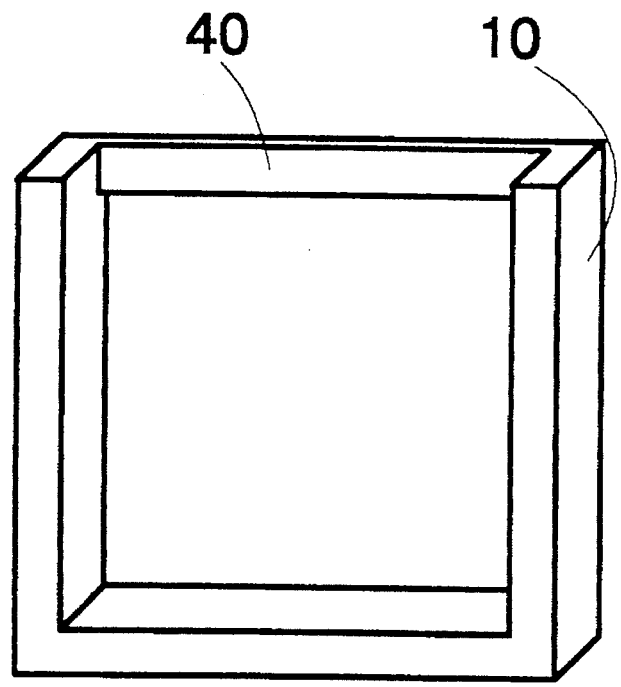
FIG. 2A and 2B show an alternative embodiment of the cassette.
Figure 2B:
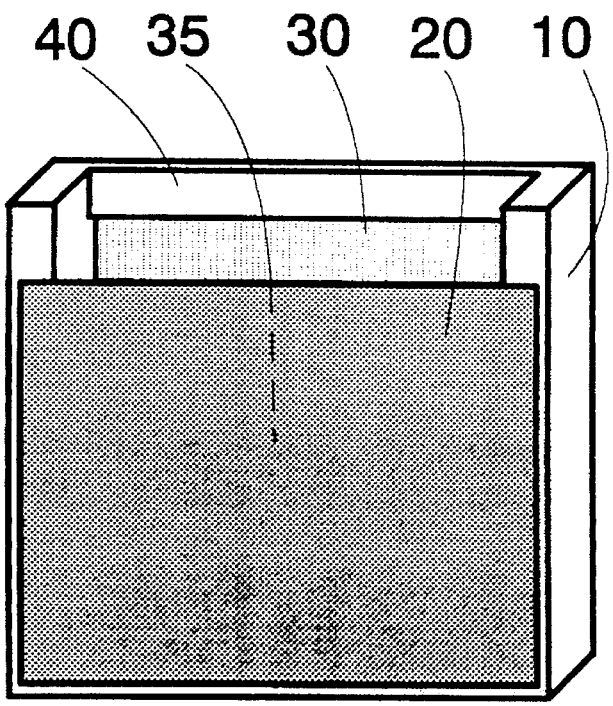

An example of the embodiments of the present invention is illustrated in FIG. 1A to 1D. It comprises three parts: a U-shaped frame 10 (FIG. 1A), a front barrier 20 (FIG. 1B), and a back barrier 30 (FIG. 1C). The barriers can be assembled to the frame by gluing. In an assembled cassette (FIG. 1D), a space inside the cassette 35 is defined by the U-shaped frame and between the barriers. The space is open to the top, through which macromolecules can be withdrawn. In an alternative embodiment, a top bar 40 is added to the frame connecting the top ends of the U-shaped frame (FIG. 2A). The top bar is thinner than the rest of the frame and the front barrier is a little shorter (FIG. 2B) so that the space inside the cassette has an opening to the top.

Frame 10 is made of an inert material, such as polypropylene, which does not easily react with chemicals. Front barrier 20, also made of an inert material, has small holes allowing macromolecules to pass through while stopping gel debris. Some of the commercially available filters are suitable, such as the HT Tuffryn membrane from Gelman Sciences (Ann Arbor, Mich.). Back barrier 30 is made of a membrane material, such as dialysis membrane (American Scientific catalog number 01614-21), that allows small molecules like salt to pass through (thus conducts electricity in electrolyte buffer) but does not allow macromolecules like DNAs, RNAs and proteins to pass through.

As indicated in FIG. 1A, the thickness of frame 10 is about 1 millimeter (mm), the height is typically 10 mm, the depth (from front to back) is about 2 mm, and the width (from left to right) ranges from 5 to 20 mm or more for collecting small or large DNA bands. The dimensions of barriers 20 and 30 match the dimensions of frame 10 so that they can be properly assembled.

OPERATION—FIGS. 3A, 3B AND 3C

Figure 3A:
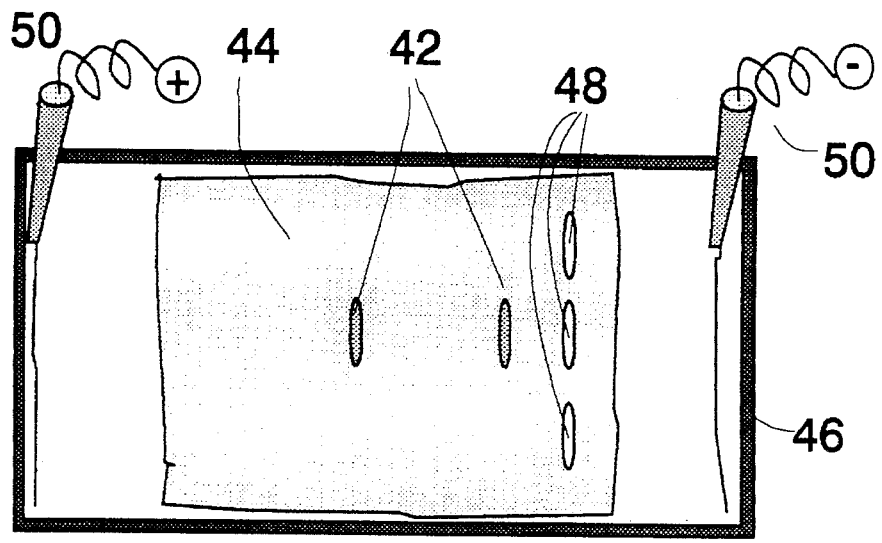
FIG. 3A, 3B and 3C illustrate the operation procedure of DNA recovery from an agarose gel using the cassette.
Figure 3B:
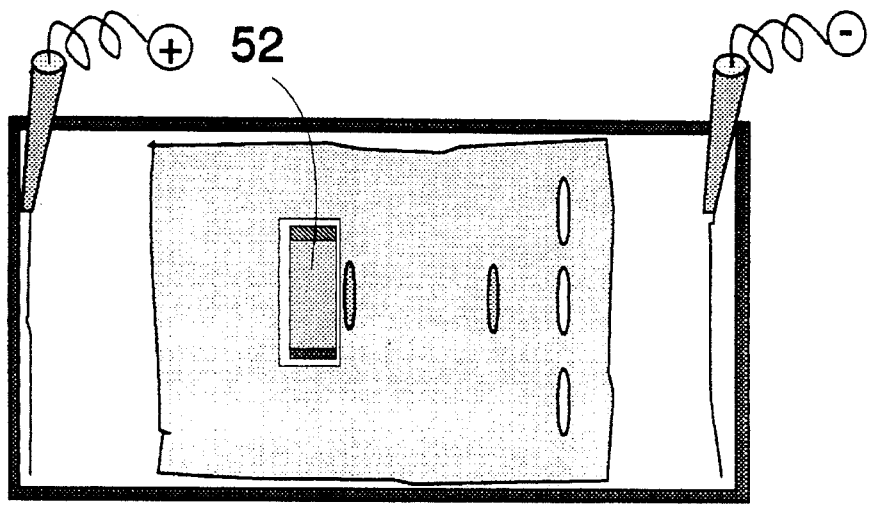
Figure 3C:
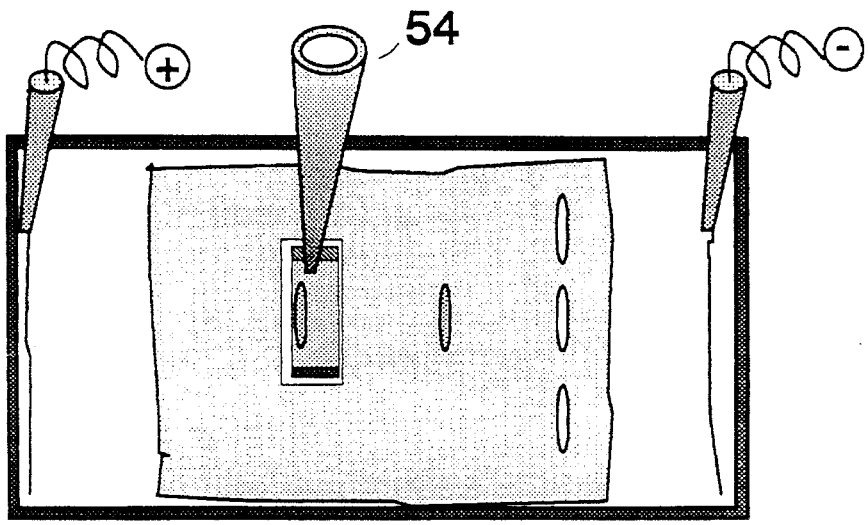

FIG. 3A shows two DNA fragments (illustrated as DNA bands 42) are separated in a piece of agarose gel 44 placed in an electrophoresis apparatus 46. DNA loading wells 48 and electrodes 50 are also shown. FIG. 3B shows that a block of gel immediately in front of the DNA band of interest is cut out and an invented elution cassette 52 is inserted into the gel. FIG. 3C shows that after a short electrophoresis, the DNA band of interest has migrated into the inserted cassette through the front barrier and is stopped by the back barrier, and a pipette 54 is used to withdraw the DNA fragment contained in the cassette between the barriers.

CONCLUSION, RAMIFICATIONS, AND SCOPE

Recovery of DNA fragments is an essential technology in molecular biology. Methods currently being used are rather complicated and time consuming. Simpler and better methods are long awaited. The current invention meets this demand. In the invention, a disposable elution cassette is designed based on the principle of electroelution. It is simpler, more convenient, easier, and faster to use, while still suitable for virtually all sizes of DNA molecules (>10 bp), suitable for small amount of DNA, and particularly appropriate for purifying larger amount of DNA fragments.

While my above description contains many specificities, these should not be construed as limitations on the scope of the invention, but rather as exemplifications of preferred embodiments thereof. Many other variations are possible. Accordingly, the scope of the invention should be determined not by the embodiment illustrated, but by the appended claims and their legal equivalents.

I claim:

1. An elution cassette for the recovery of macromolecules including DNAs, RNA, and proteins, comprising:

(a) a frame having front and rear portions, (b) a first barrier consisting of filter materials which allows macromolecule to pass through while stopping gel debris attached to said front portion of said frame, (c) a second barrier consisting of a membrane material which allows small ions to pass through but does not allow macromolecules to pass through attached to said rear portion of said frame, (d) a space inside the cassette defined by said frame and said barriers, wherein said space has at least one opening to the top for recovering said macromolecules, whereby when said cassette with said barriers is placed into an electrophoresis apparatus, macromolecules driven by an electric field migrate into said space in the cassette through said front barrier and are stopped by said rear barrier.

2. The cassette of claim 1 wherein said frame has a U shape.

3. The cassette of claim 2 wherein said U-shaped frame has a top bar added connecting the top ends of said U-shaped frame.

* * * * *